(12) United States Patent
Jiang et al.

(10) Patent No.: US 12,165,861 B2
(45) Date of Patent: *Dec. 10, 2024

(54) MASS SPECTROMETRY METHOD FOR MEASURING VITAMIN B6 IN BODY FLUID

(71) Applicant: Quest Diagnostics Investments Incorporated, Wilmington, DE (US)

(72) Inventors: Qibo Jiang, Los Angeles, CA (US); Sum Chan, San Clemente, CA (US); Richard E Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/466,168

(22) Filed: Sep. 13, 2023

(65) Prior Publication Data

US 2023/0420235 A1 Dec. 28, 2023

Related U.S. Application Data

(63) Continuation of application No. 16/996,108, filed on Aug. 18, 2020, now Pat. No. 11,798,794, which is a continuation of application No. 14/991,987, filed on Jan. 10, 2016, now abandoned, which is a continuation of application No. 13/208,295, filed on Aug. 11, 2011, now Pat. No. 9,234,901, which is a continuation of application No. 11/763,380, filed on Jun. 14, 2007, now Pat. No. 8,017,403.

(51) Int. Cl.
*G01N 33/82* (2006.01)
*G01N 30/72* (2006.01)
*G01N 33/49* (2006.01)
*H01J 49/00* (2006.01)
*G01N 30/02* (2006.01)

(52) U.S. Cl.
CPC .......... *H01J 49/0031* (2013.01); *G01N 33/49* (2013.01); *G01N 33/82* (2013.01); *H01J 49/004* (2013.01); *Y10T 436/145555* (2015.01)

(58) Field of Classification Search
CPC ....... G01N 33/49; G01N 33/82; H01J 49/004; H01J 49/0031; Y10T 436/145555
See application file for complete search history.

(56) References Cited

U.S. PATENT DOCUMENTS 5,772,874 A 6/1998 Quinn et al.
5,795,469 A 8/1998 Quinn et al.
(Continued)

FOREIGN PATENT DOCUMENTS

WO WO-2006096691 A1 9/2006

OTHER PUBLICATIONS

Adams J.B., et al., "Abnormally High Plasma Levels of Vitamin B6 in Children with Autism Not Taking Supplements Compared to Controls Not Taking Supplements," Journal of Alternative and Complementary Medicine, 2006, vol. 12 (1), pp. 59-63.
(Continued)

*Primary Examiner* — Rebecca M Fritchman
(74) *Attorney, Agent, or Firm* — Foley & Lardner LLP

(57) ABSTRACT

Provided are methods of detecting the presence or amount of the active form of vitamin B6, pyridoxal 5'-phosphate, in a body fluid sample using tandem mass spectrometry coupled with liquid chromatography.

10 Claims, 3 Drawing Sheets

(56) References Cited

U.S. PATENT DOCUMENTS

| | | | |
|---|---|---|---|
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 6,312,893 | B1 | 11/2001 | Van Ness et al. |
| 6,348,688 | B1 | 2/2002 | Vestal |
| 7,087,395 | B1 | 8/2006 | Garrity et al. |
| 8,017,403 | B2 | 9/2011 | Jiang et al. |
| 9,234,901 | B2 | 1/2016 | Jiang et al. |
| 2005/0070023 | A1* | 3/2005 | Nguyen ............. G01N 30/7206 436/129 |
| 2006/0105392 | A1 | 5/2006 | Lehmann et al. |
| 2006/0228809 | A1 | 10/2006 | Clarke et al. |

OTHER PUBLICATIONS

Argoudelis C.J., et al., "Simple Isocratic High-Performance Liquid Chromatographic Method for the Separation of the Six Vitamers of Vitamin B6," Journal of Chromatography B, 1988, vol. 424 (2), pp. 315-323.

Bailey A.L., et al., "High Performance Liquid Chromatography Method for the Determination of Pyridoxal-5-Phosphate in Human Plasma: How Appropriate are Cut-Off Values for Vitamin B6 Deficiency?," European Journal of Clinical Nutrition, 1999, vol. 53 (6), pp. 448-455.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Bisp M.R, et al., "Determination of Vitamin B6 Vitamers and Pyridoxic Acid in Plasma: Development an Devaluation of a High-Performance Liquid Chromatographic Assay," Analytical Biochemistry, 2002, vol. 305 (1), pp. 82-89.

Bonne M., et al., Mass Spectrometry-Mass Spectrometry. Mar. 2007. Retrieved from the Internet: URL:www.cpe.fr/ciufolini/msms.htm.

Botticher B., et al., "A New HPLC-Method for the Simultaneous Determination of B1-, B2- and B6-Vitamers in Serum and Whole Blood," International Journal for Vitamin and Nutrition Research, 1987, vol. 57 (3), pp. 273-278.

Coburn S.P., et al., "A Versatile Cation-Exchange Procedure for Measuring the Seven Major Forms of Vitamin B.Sub.6 in Biological Samples," Analytical Biochemistry, 1983, vol. 129 (2), pp. 310-317.

Dear G.J., et al., "Use of Directly Couple Ion-Exchange Liquid Chromatography-Mass Spectrometry and Liquid Chromatography-Nuclear Magnetic Resonance Spectroscopy as a Strategy for Polar Metabolite Identification," Journal of Chromatography B, 2000, vol. 748 (1), pp. 295-309.

Du L., et al., "High Turbulence Liquid Chromatography Online Extraction and Tandem Mass Spectrometry for the Simultaneous Determination of Suberoylanilide Hydroxamic Acid and its Two Metabolites in Human Serum," Rapid Communications in Mass Spectrometry, 2005, vol. 19 (13), pp. 1779-1787.

Eckers C., et al., "Combined liquid chromatography-mass spectrometry of drugs. in Therapeutic Drug Monitoring and Toxicology by Liquid Chromatography", Steven H.Y.eds, Marcel Dekker, Inc., 1985, vol. 32, Chapter 6, pp. 115-149.

Edwards P., et al., "A Simple Liquid-Chromatographic Method for Measuring Vitamin B6 Compounds in Plasma," Clinical Chemistry, 1989, vol. 35 (2), pp. 241-245.

Examiner's Answer to Appeal Brief mailed Mar. 27, 2019 for U.S. Appl. No. 14/991,987, filed Jan. 10, 2016.

Final Office Action mailed Apr. 3, 2012 for U.S. Appl. No. 13/208,295, filed Aug. 11, 2011.

Final Office Action mailed Feb. 7, 2022 for U.S. Appl. No. 16/996,108, filed Aug. 18, 2020.

Final Office Action mailed Sep. 14, 2017 for U.S. Appl. No. 14/991,987, filed Jan. 10, 2016.

Final Office Action mailed Oct. 19, 2009 for U.S. Appl. No. 11/763,380, filed Jun. 14, 2007.

Guo T., et al., "Simultaneous Determination of 12 Steroids by Isotope Dilution Liquid Chromatography-Photospray Ionization Tandem Mass Spectrometry," Analytica Chimica Acta, 2006, vol. 372 (1-2), pp. 76-82.

Guzzetta A., Reverse Phase HPLC Basics for LC/MS [Online], Jul. 2001.Retrieved from the Internet:[URL: http://www.ionsource.com/tutorial/chromatography/rphplc.htm].

Hachey D.L., et al., "Quantitation of Vitamin B6 in Biological Samples by Isotope Dilution Mass Spectrometry," Analytical Biochemistry, 1985, vol. 151 (1), pp. 159-168.

International Search Report for Application No. PCT/US08/66609, mailed on Sep. 17, 2008, 1 Page.

Jemal M., et al., "High-Throughput Quantitative Bioanalysis by LC/MS/MS," Biomedical Chromatography, 2000, vol. 14 (6), pp. 422-429.

Keevil B.G., et al., "Quantification of Urinary Oxalate by Liquid Chromatography-Tandem Mass Spectrometry with Online Weak Anion Exchange Chromatography," Clinical Chemistry, 2006, vol. 52 (12), pp. 2296-2299.

Kimura M., et al., "Highly Sensitive and Simple Liquid Chromatographic Determination in Plasma of B6 Vitamers, Especially Pyridoxal 5'-Phosphate," Journal of Chromatography A, 1996, vol. 722 (1-2), pp. 295-301.

Lachance et al., "A Fast On-Line HTLC-MS/MS Method for the Simultaneous Bioanalytical Validation of a Drug in Multiple Animal Species", Proceedings of the 50.sup.th ASMS Conference on Mass Spectrometry and Allied Topics, Orlando, FL, Jun. 2-6, 2002.

Merchant M., et al., "Recent Advancements in Surface-Enhanced Laser Desorption/Ionization-Time of Flight-Mass Spectrometry," Electrophoresis, 2000, vol. 21 (6), pp. 1164-1167.

Midttun O., et al., "Multianalyte Quantification of Vitamin B6 and B2 Species in the Nanomolar Range in Human Plasma by Liquid Chromatography-Tandem Mass Spectrometry," Clinical Chemistry, 2005, vol. 51 (7), pp. 1206-1216.

Non-Final Office Action mailed Feb. 2, 2023 for U.S. Appl. No. 16/996,108, filed Aug. 18, 2020.

Non-Final Office Action mailed Sep. 15, 2010 for U.S. Appl. No. 11/763,380, filed Jun. 14, 2007.

Non-Final Office Action mailed Jan. 19, 2017 for U.S. Appl. No. 14/991,987, filed Jan. 10, 2016.

Non-Final Office Action mailed Dec. 22, 2008 for U.S. Appl. No. 11/763,380, filed Jun. 14, 2007.

Non-Final Office Action mailed Jan. 22, 2016 for U.S. Appl. No. 14/063,956, filed Oct. 25, 2013.

Non-Final Office Action mailed Oct. 24, 2011 for U.S. Appl. No. 13/208,295, filed Aug. 11, 2011.

Non-Final Office Action mailed Jul. 27, 2021 for U.S. Appl. No. 16/996,108, filed Aug. 18, 2020.

Notice of Allowance mailed Jun. 20, 2023 for U.S. Appl. No. 16/996,108, filed Aug. 18, 2020.

Patent Board Decision—Examiner Affirmed mailed Jun. 18, 2020 for U.S. Appl. No. 14/991,987, filed Jan. 10, 2016.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography-Mass Spectrometry," Analytical Chemistry, 2000, vol. 72 (15), pp. 3653-3659.

Rybak M.E., et al., "Clinical Vitamin B-6 Analysis: An Interlaboratory Comparison of Pyridoxal 5-Phosphate Measurements in Serum," Clinical Chemistry, 2005, vol. 51 (7), pp. 1223-1231.

Schrijver J., et al., "Semi-Automated Fluorometric Determination of Pyridoxal-5'-Phosphate (Vitamin B6) in Whole Blood by High-Performance Liquid Chromatography (HPLC)," International Journal for Vitamin and Nutrition Research, 1981, vol. 51 (3), pp. 216-222.

Stokvis E., et al., "Stable Isotopically Labeled Internal Standards in Quantitative Bioanalysis Using Liquid Chromatography/Mass Spec-

(56) References Cited

OTHER PUBLICATIONS trometry: Necessity or Not," Rapid Communication in Mass Spectrometry, 2005, vol. 19, pp. 401-407.
Supplementary European Search Report for Application No. EP08770752, mailed on Jul. 19, 2010, 8 pages.
Talwar D., et al., "Pyridoxal Phosphate Decreases in Plasma but Not Erythrocytes During Systemic Inflammatory Response," Clinical Chemistry, 2003, vol. 49 (3), pp. 515-518.
Ubbink B., et al., "Stability of Pyridoxal-5-Phosphate Semicarbazone: Applications in Plasma Vitamin B6 Analysis and Population Surveys of Vitamin B6 Nutritional Status," Journal of Chromatography, 1985, vol. 342, pp. 277-284.
Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.
Written Opinion for Application No. PCT/US2008/66609 mailed on Sep. 17, 2008, 4 pages.
Zafra-Gomez A., et al., "Simultaneous Determination of Eight Water-Soluble Vitamins in Supplemented Foods by Liquid Chromatography," Journal of Agricultural and Food Chemistry, 2006, vol. 54 (13), pp. 4531-4536.
Zdravkovic M., et al., "The Effects of NN414, a SUR1/Kir6.2 Selective Potassium Channel Opener, in Healthy Male Subjects," The Journal of Clinical Pharmacology, 2005, vol. 45, pp. 763-772.
Zeng W., et al., "A Direct Injection High-Throughput Liquid Chromatography Tandem Mass Spectrometry Method for the Determination of a New Orally Active Alphavbeta3 Antagonist in Human Urine and Dialysate," Rapid Communications in Mass Spectrometry, 2003, vol. 17 (22), pp. 2475-2482.
Zeng W., et al., "Determination of MK-0431 in Human Plasma Using High Turbulence Liquid Chromatography Online Extraction and Tandem Mass Spectrometry," Rapid Communications in Mass Spectrometry, 2006, vol. 20 (8), pp. 1169-1175.
Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

\* cited by examiner

MASS SPECTROMETRY METHOD FOR MEASURING VITAMIN B6 IN BODY FLUID

CROSS REFERENCE TO RELATED PATENT APPLICATIONS

This application is a continuation application of U.S. application Ser. No. 16/996,108, filed Aug. 18, 2020, which is a continuation application of U.S. application Ser. No. 14/991,987, filed Jan. 10, 2016, which is a continuation application of U.S. application Ser. No. 13/208,295, filed Aug. 11, 2011, now U.S. Pat. No. 9,234,901, which is a continuation application of U.S. application Ser. No. 11/763,380, filed Jun. 14, 2007, now U.S. Pat. No. 8,017,403, each of which is hereby incorporated by reference in its entirety.

FIELD OF THE INVENTION

The invention relates to the detection of the active form of vitamin B6, pyridoxal 5'-phosphate (PLP), by tandem mass spectrometry (MS-MS) coupled with liquid chromatography.

BACKGROUND OF THE INVENTION

Documents cited in this description are denoted numerically, in parentheses, by reference to a bibliography below. None of the cited references is admitted prior art.

Vitamin B6 is a water-soluble vitamin existing in seven forms: pyridoxine (PN), pyridoxine 5'-phosphate (PNP), pyridoxal (PL), pyridoxal 5'-phosphate (PLP), pyridoxamine (PM), pyridoxamine 5'-phosphate (PMP), and 4-pyridoxic acid (PA). All forms except for PA are interconvertible in vivo. PN, PL and PM are natural compounds in food, which after absorption, are phosphorylated to an active form, to PNP, PLP, and PMP. PLP functions as a cofactor amino acid metabolism. PN is the form provided as vitamin B6 supplement. Under normal conditions, a 100 mg of vitamin B6 will produce a plasma peak in 2 hours with a half-life of 8 hours. Doses of over 25 mg produce little change in plasma PLP. PA is the ultimate metabolite of vitamin B6, which is excreted in the urine.

Vitamin B6 plays an important role in the metabolism of amino acids, lipids, carbohydrates, and neurotransmitters. For instance, vitamin B6 functions as a coenzyme for a number of key enzymes, such as kynureninase, which catalyzes the synthesis of niacin from tryptophan; δ-aminolevulinic acid synthetase, which catalyzes heme synthesis; and glycogen phosphorylase, which catalyzes the release of glucose stored in the muscle as glycogen. Vitamin B6 also participates in neurotransmitter synthesis and amino acid synthesis, as well as the catabolism of homocysteine to cystathionine and cystathionine to cysteine, which involves a pathway closely related to increased homocysteine levels.

Vitamin B6 deficiency causes weakness, susceptibility to infection, sleeplessness, depression, dermatitis, glossitis, stomatitis and seizures. Chronic vitamin B6 deficiency may even cause severe nerve compression disorders. A low blood vitamin B6 level is considered a risk factor for cardiovascular diseases. Although vitamin B6 deficiency is rare as a low-intake malnutrition in the United States, it is commonly associated with other diseases, such as alcoholism, cirrhosis, kidney failure, and small intestinal malabsorption, etc. Therefore, it is important to detect the active form of vitamin B6, PLP, in plasma to determine vitamin B6 deficiency or overdosage, thereby evaluating wellness and monitoring treatment.

Conventionally, the level of aspartate aminotransferase is measured in red blood cells to diagnose vitamin B6 deficiency. This test, however, is a functional assay rather than a direct measurement of the PLP status (Ref 1).

Clinical analysis of plasma PLP concentrations is a direct measurement of the active form of vitamin B6 in the blood. A number of publications report successful detection of plasma PLP by high-performance liquid chromatographic assay (HPLC) (Refs. 2-8). Hachey et al. describe determination of vitamin B6 in biological samples by mass spectrometry (Ref. 9). Liquid chromatography-tandem mass spectrometry can be used to measure vitamin B6 in human plasma (Ref. 10). Nevertheless, Rybak et al. report that there is an observed imprecision among the existing HPLC-based and enzymatic vitamin B6 assays (Ref 24).

SUMMARY OF THE INVENTION

The present invention relates to detecting the presence or amount of the active form of vitamin B6, pyridoxal 5'-phosphate (PLP), in a body fluid sample by tandem mass spectrometry (MS-MS) coupled with liquid chromatography. Preferably, the invention relates to detecting the presence or amount of PLP in plasma.

In certain embodiments, a body fluid sample is a sample obtained from a mammalian animal, such as a dog, cat, horse, etc. Particular preferred mammalian animals are primates, most preferably humans. Suitable samples include blood, plasma, serum, urine, saliva, tears, and cerebrospinal fluid. Preferably, the sample is a plasma sample. Such samples may be obtained, for example, from a patient; that is, a living person in a clinical setting for diagnosis, prognosis, or treatment of a disease or condition.

In one aspect, the invention provides a method for detecting the presence or amount of PLP in a body fluid sample by tandem mass spectrometry. The method include the steps of (i) purifying said sample by liquid chromatography; (ii) generating a parent ion of PLP from the purified sample; (iii) generating one or more daughter ions of the parent ion; and (iv) detecting the presence or amount of one or more ions generated in step (ii) or step (iii) or both, and relating the detected ions to the presence or amount of PLP in the sample. In certain embodiments, the method is used to detect the presence or amount of PLP in plasma. In a preferred embodiment, the PLP in the sample is ionized by electrospray.

In preferred embodiments, a separately detectable internal standard is provided in the sample, the presence or amount of which is also detected in the sample. In these embodiments, both PLP and the internal standard present in the sample are purified and then ionized to produce a plurality of ions detectable in a mass spectrometer operating in positive ion mode, and one or more ions produced from each are detected by mass spectrometry.

The term "operating in positive ion mode" refers to those mass spectrometry methods where positive ions are detected. Similarly, "operating in negative ion mode" refers to those mass spectrometry methods where negative ions are detected.

In preferred embodiments, the PLP ions detectable in a mass spectrometer include ions with a mass/charge ratio (m/z) of 248.03+/−1 m/z for the parent ion and 150.00+/−1 m/z for the daughter ion. The variation in the m/z value observed by mass spectrometry for the parent and daughter ion(s) generally ranges from 0.001 to 1 m/z unit of the atomic mass. For example, the variation in mass observed using different mass spectrometers for identifying the parent 248.03 ion should be within 1 m/z which is a range between 247.03 m/z and 249.03 m/z.

A preferred internal standard is 2-hydroxy-6-methylpyridine-3-carboxylic acid (Aldrich). In preferred embodiments, the internal standard detectable in a mass spectrometer has a mass/charge ratio (m/z) of 154.04+/−1 m/z for the parent ion and 136.00+/−1 m/z for the daughter ion. An alternative internal standard for the assay is isotopically labeled vitamin B6.

If multiple daughter ions are monitored, the ion ratio variation of mass transitions of different daughter ions generated from the same parent ion should not exceed+/−25%, in accordance with the College of American Pathologists (CAP) standards. For example, if a compound generates daughter ions A and B from the same parent ion, the ion ratio is (the intensity of ion A divided by the intensity of ion B)×100.

In other preferred embodiments, the purifying step involves (a) applying a body fluid sample to an extraction column; (b) washing the extraction column under conditions whereby pyridoxal 5'-phosphate is retained by the column; (c) eluting retained material comprising pyridoxal 5'-phosphate from the extraction column; (d) applying the extraction column-eluted material comprising pyridoxal 5'-phosphate to an analytical column; and (e) eluting purified pyridoxal 5'-phosphate from the analytical column. In preferred embodiments, the extraction column is a large particle extraction column, and the analytical column is a C-8 analytical column. In other embodiments, the extraction column is a turbulent flow liquid chromatography column, and more preferably a high turbulent flow liquid chromatography column (HTLC).

By "large particle" column, is meant a column containing an average particle diameter greater than about 35 In the preferred embodiment, the extraction column contains particles of about 50 μm in diameter, and the C-8 analytical column comprises particles of about 3.5 μm in diameter. As used in this context, the term "about" means±10%. Preferably, the extraction column is a mixed mode anion exchange polymer column with 0.5 (ID)×50 mm, 50μ particle size.

The term "analytical column" as used herein refers to a chromatography column having sufficient chromatographic "plates" to effect a separation of materials in a sample that elute from the column sufficient to allow a determination of the presence or amount of an analyte. Such a column is often distinguished from an "extraction column," which has the general purpose of separating or extracting retained material from non-retained materials in order to obtain a purified sample for further analysis. A preferred analytical column is an HPLC column.

The summary of the invention described above is non-limiting and other features and advantages of the invention will be apparent from the following detailed description of the invention, and from the claims.

| | |
|---|---|
| m/z values of parent/daughter ions: | 248.03/150.00 amu; |
| SW: | 500.00; |
| View width (minutes): | 3.75 |

-continued

| | |
|---|---|
| RT reference (RTR): | Yes; |
| Minimum peak height (MPH, signal/noise ratio): | 3.0; |
| Smooth: | 5; |
| Peak detection algorithm (PDA): | genesis. |

Figure 1:
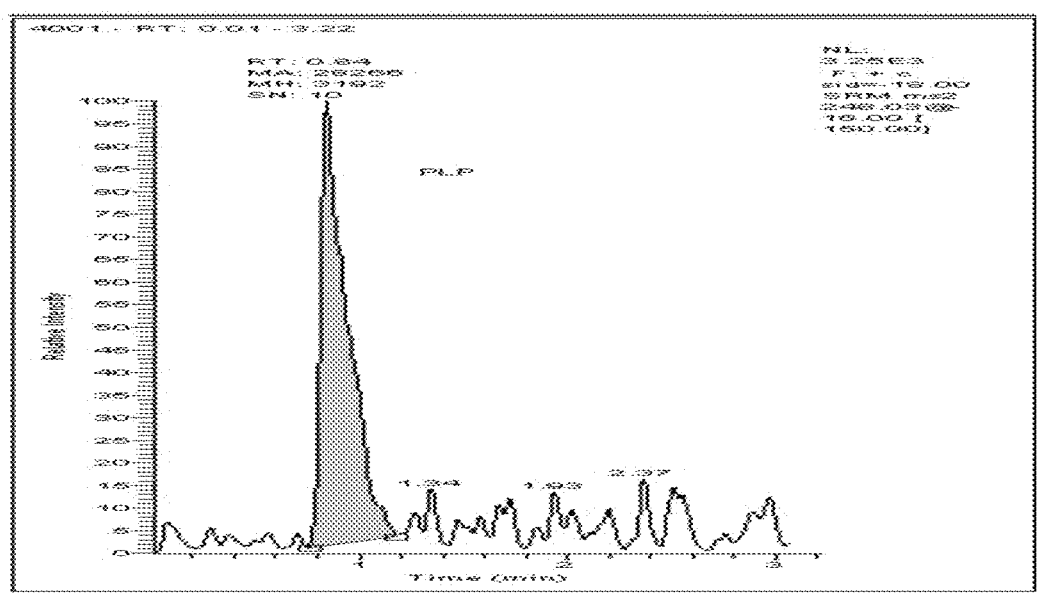
FIG. 1 is a chromatogram of PLP in EDTA-plasma upon tandem mass spectrometry analysis at the following integration parameters.

The chromatogram is produced by the manufacturer-provided software (Aria version 1.5, Cohesive Technologies) using the peak intensity (area counts) from the mass spectrometry. As shown in the FIG. 1, the highest peak of PLP appears at an estimated retention time of 0.75 minute.

Figure 2:
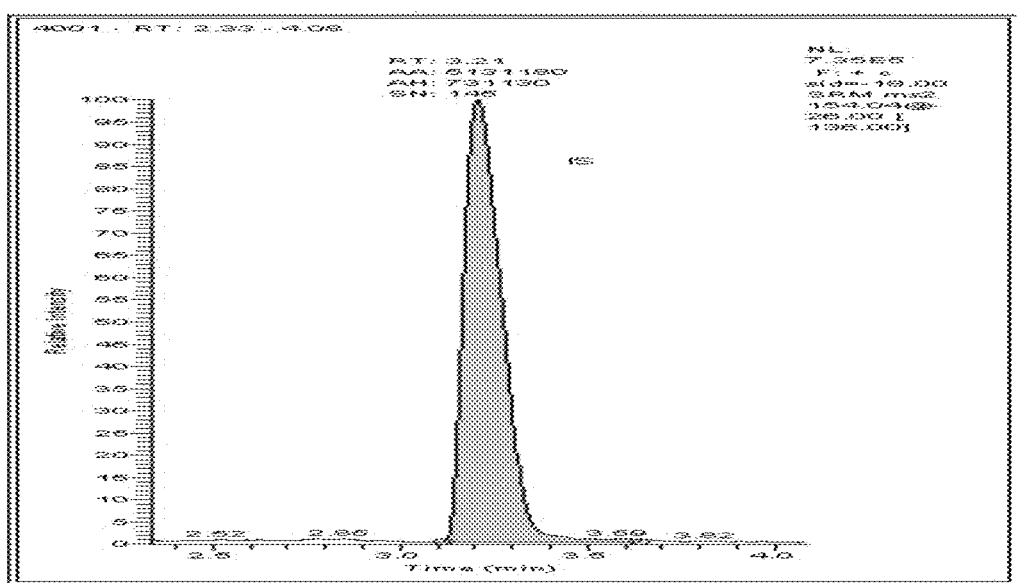

FIG. 2 is a chromatogram of the internal standard, 2-hydroxy-6-methylpyridine-3-carboxylic acid, upon tandem mass spectrometry analysis at the following integration parameters:

| | |
|---|---|
| m/z values of parent/daughter ions: | 154.04/136.00 amu; |
| SW: | 50.00; |
| View width (minutes): | 3.75 |
| RT reference (RTR): | Yes; |
| Minimum peak height (MPH, signal/noise ratio): | 3.0; |
| Smooth: | 5; |
| Peak detection algorithm (PDA): | genesis. |

The internal standard is added to each sample in equal amount for each process. As shown in the FIG. 1, the highest peak of 2-hydroxy-6-methylpyridine-3-carboxylic acid appears at an estimated retention time of 3.16 minute.

Figure 3:
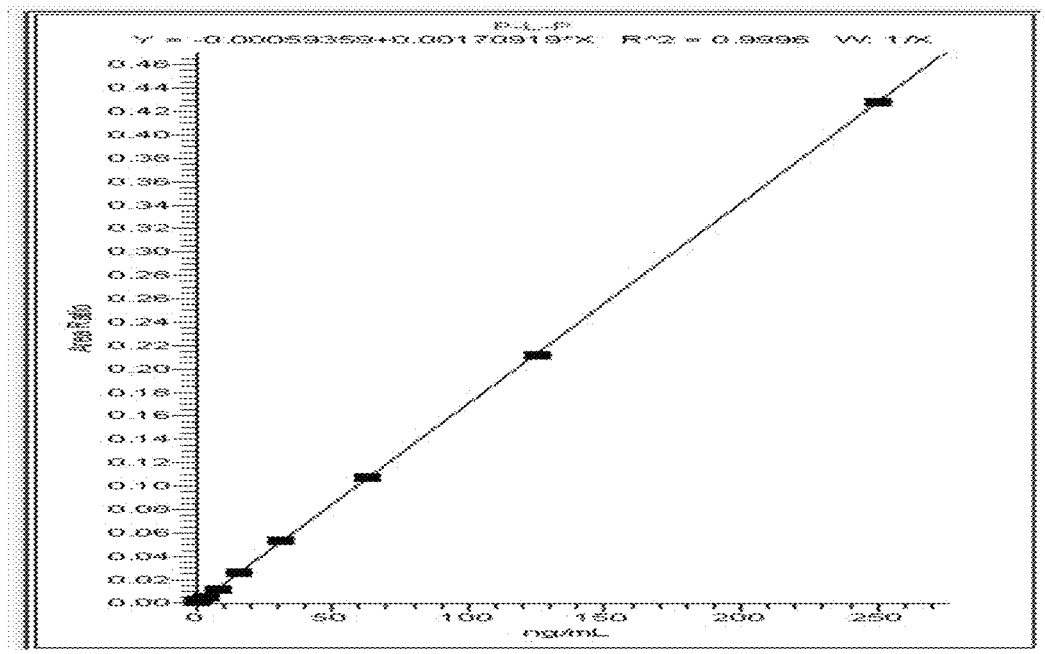

FIG. 3 depicts the typical standard curve of PLP. The software uses peak area ratio of PLP over its internal standard for data reduction. The peak areas of internal standard are consistent (within +/−30%) for all the samples tested, and the concentration levels of PLP correspond to the peak area ratios of PLP vs. internal standard. The peak area ratio obtained from MS/MS is plotted against various known PLP concentrations between 2 ng/mL and 250 ng/mL to obtain the standard curve. A blank plasma or serum as zero standard is included. Linear regression with 1/x weighting is used for data reduction.

DETAILED DESCRIPTION OF THE PREFERRED EMBODIMENTS

The present invention describes methods for detecting the presence or amount of the active form of vitamin B6, PLP, in a sample. The methods utilize liquid chromatography to perform an initial purification of PLP followed by tandem mass spectrometry (MS/MS), thereby providing a high-throughput assay system for detecting and quantifying PLP in a liquid sample. The assay offers enhanced specificity and is accomplished in less time and with less sample preparation than required by other vitamin B6 assays. In various embodiments the methods of the invention accurately quantify PLP in samples where it is present in the range between 2 ng/mL and 250 ng/mL, while the method is sufficiently sensitive to detect PLP at a concentration as low as 0.96 ng/ml.

Sample Purification by HTLC/HPLC

Preferably, PLP is initially purified by high turbulence-flow liquid chromatography (HTLC) and high performance liquid chromatography (HPLC) prior to mass spectrometry. "Purification" in this context does not refer to removing all materials from the sample other than the analyte(s) of interest. Instead, purification refers to a procedure that enriches the amount of one or more analytes of interest relative to one or more other components of the sample. In preferred embodiments, purification can be used to remove one or more interfering substances, e.g., one or more substances that would interfere with detection of an analyte ion by mass spectrometry.

HTLC is a form of chromatography that utilizes turbulent flow of the material being assayed through the column packing as the basis for performing the separation. HTLC has been applied in the preparation of samples containing two unnamed drugs prior to analysis by mass spectrometry (Refs. 11-15). Persons of ordinary skill in the art understand "turbulent flow." When fluid flows slowly and smoothly, the flow is called "laminar flow." In laminar flow the motion of the particles of fluid is orderly with particles moving generally in straight lines. In contrast, at faster velocities, the inertia of the water overcomes fluid frictional forces and turbulent flow results. Fluid not in contact with the irregular boundary "outruns" that slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (Refs. 16 & 17).

Traditional HPLC analysis relies on the chemical interactions between sample components and column packings, in which laminar flow of the sample through the column is the basis for separation of the analyte of interest from the sample. The skilled artisan will understand that separation in such columns is a partition process. In contrast, it is believed that "turbulent flow," such as that provided by HTLC columns and methods, may enhance the rate of mass transfer, thereby improving the separation characteristics provided by the separation system. HTLC columns separate components by means of high chromatographic flow rates through a packed column containing rigid particles. By employing high flow rates (e.g., 3-4 ml/min), turbulent flow occurs in the column that causes nearly complete interaction between the stationary phase and the analytes. An additional advantage of HTLC columns is that the macromolecular build-up associated with biological fluid matrices is avoided since the high molecular weight species are not retained under the turbulent flow conditions.

Because HTLC method can combine multiple separations in one automated procedure, it not only lessens the need for lengthy sample preparation and operates at a significantly greater speed, but also eliminates the opportunity for operator error by minimizing operator involvement during the purification. Such a method also achieves a separation performance superior to laminar flow (HPLC) chromatography. HTLC allows for direct injection of biological samples (plasma, urine, etc.). This is difficult to achieve in traditional forms of chromatography because denatured proteins and other biological debris quickly block the separation columns.

Additionally, the commercial availability of HTLC apparatuses that permit multiplexing of columns and direct integration with MS instruments makes such instruments particularly well suited to high-throughput applications.

During chromatography, the separation of materials is effected by variables such as choice of eluant (also known as a "mobile phase"), choice of gradient elution and the gradient conditions, temperature, etc.

The present invention applies a complex gradient for HTLC and HPLC chromatography. More specifically, the gradient starts with pumping 100% deionized water at 0.4 mL/minute on the HTLC column and 5% acetic acid at 0.4 mL/minute on the HPLC column for 60 seconds. The sample is injected at the same time as the gradient begins. Subsequently, the HTLC column is washed with 100% deionized water at a flow rate of 1.5 mL/minute for 50 seconds, followed by 5% aqueous acetic acid at the same rate for 40 seconds. The extract is eluted from the HTLC column to the HPLC column with 5% aqueous acetic acid at a flow rate of 0.4 mL/minute for 200 seconds, starting at 2 minutes calculated from sample injection. Afterwards, the elution from the HPLC column is driven by a gradient of 5% aqueous acetic acid/acetonitrile (45 to 15%/55 to 85%) at a flow rate of 0.4 mL/minute. The reminder of the gradient time is for column cleaning and re-equilibration with deionized water, 5% aqueous acetic acid and acetonitrile. The total duration for chromatograph is 9.0 minutes, with 4.3-minute data window for each sample. Therefore, two samples can be analyzed within the 9-minute method time when the dual channels are operated with overlapping gradients.

In certain embodiments, an analyte may be purified by applying a body fluid sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. The second mobile phase may be phased in gradually, usually under computer control directing the composition of mobile phase over time, or by an immediate change in the mobile phase. The retained materials may also be removed from the column by "backflushing" the column, or reversing the direction of flow of the mobile phase. This may be particularly convenient for material that is retained at the top of the column. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample.

In a preferred embodiment, PLP is initially purified by liquid chromatography, which involves the steps of (a) applying a body fluid sample to an extraction column; (b) washing the extraction column under conditions whereby pyridoxal 5'-phosphate is retained by the column; (c) eluting retained material comprising pyridoxal 5'-phosphate from the extraction column; (d) applying the extraction column eluted material comprising pyridoxal 5'-phosphate to an analytical column; and (e) eluting purified pyridoxal 5'-phosphate from the analytical column. Preferably, the extraction column is an HTLC column and the analytical column is an HPLC column.

In various embodiments, one or more of the purification and/or analysis steps can be performed in an online, automated fashion. For example, in one embodiment, the purification steps (a)-(e) are performed in an online, automated fashion. In another embodiment, the steps of mass spectrometry are performed online following steps (a)-(e). The term "online, automated fashion" as used herein refers to steps performed without the need for operator intervention. For example, by careful selection of valves and connector plumbing, two or more chromatography columns can be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an online fashion to the detector system, e.g., an MS system. Thus, an operator may place a tray of samples in an autosampler, and the remaining operations are performed under computer control, resulting in purification and analysis of all samples selected.

In contrast, the term "off-line" as used herein refers to a procedure requiring manual intervention of an operator after the sample is loaded onto the first column. Thus, if samples are subjected to precipitation, and the supernatants are then manually loaded into an autosampler, the precipitation and loading steps are off-line from the subsequent steps.

Sample Analysis by MS/MS

Purified sample is subjected to ionization before analyzed by MS/MS. As used herein, the term "ionization" refers to the process of generating an analyte ion having a net electrical charge equal to one or more electron units. Negative ions are those having a net negative charge of one or more electron units, while positive ions are those having a net positive charge of one or more electron units.

The term "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z") (Refs. 18-23).

The ions may be detected using several detection modes. For example, selected ions may be detected using a selective ion monitoring mode (SIM), or alternatively, ions may be detected using a scanning mode, e.g., multiple reaction monitoring (MRM) or selected reaction monitoring (SRM).

Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

"Tandem mass spectrometry," or "MS/MS" is employed to enhance the resolution of the MS technique. In tandem mass spectrometry, a parent ion (a.k.a. precursor ion) generated from a molecule of interest may be filtered in an MS instrument, and the parent ion subsequently fragmented to yield one or more daughter ions (a.k.a. fragment or product ions) that are then analyzed in a second MS procedure.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased vibrational energy.

By careful selection of parent ions, only ions produced by certain analytes of interest are passed to the fragmentation chamber to generate the daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

The mass spectrometer typically provides the user with an ion scan; that is, the relative abundance of each m/z over a given range (e.g., 100 to 900 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of PLP. Numerous other methods for relating the presence or amount of an ion to the presence or amount of the original molecule are well known to those of ordinary skill in the art.

The skilled artisan will understand that the choice of ionization method can be determined based on the analyte to be measured, type of sample, the type of detector, the choice of positive versus negative mode, etc. Ions can be produced using a variety of methods including, but not limited to, electron ionization, chemical ionization, fast atom bombardment, field desorption, and matrix-assisted laser desorption ionization (MALDI), surface enhanced laser desorption ionization (SELDI), photon ionization, electrospray ionization, and inductively coupled plasma. Electrospray ionization is a preferred ionization method. The term "electrospray ionization," or "ESI," as used herein refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The concentration of PLP in the plasma between 3 and 35 ng/mL established by radioenzymatic assay (REA) for a child of 2-17 years old, or between 3 and 26 ng/mL established by REA for an adult of 18 years or older, is within the normal range. The adult reference values obtained by REA are correlated well with those obtained by the LC-MS-MS method of the invention. A slope of 0.9745 is observed, i.e. the values obtained by the LC-MS-MS method are 2.6% higher than the REA values statistically.

The following examples serve to illustrate the invention. These examples are in no way intended to limit the scope of the invention.

Example 1. Sample Preparation

A. Plasma Sample

The blood is collected in EDTA from a subject following an overnight fast. The subject should be restricted from alcohol and vitamins consumption for 24 hours before sample collection. Plasma should be separated from cells immediately upon collection of blood or within 6 hours from the whole blood that is kept refrigerated and protected from light.

The cells are separated by centrifugation at 2-8° C. at 2,200-2,500 rpm, 800-1000 g for 5-10 minutes. Then the plasma is transferred to a dark-brown polypropylene or polyethylene transport tube to protect it from light. Alternately, a neutral color polypropylene or polyethylene tube can be used if it is wrapped in aluminum foil. Freeze the tube at −10 to −30° C. The samples are acceptable if they are kept at −10 to −30° C. for 6 days, or at −60 to −80° C. for 6 weeks.

B. Internal Standard Stock and Working Solutions

An internal standard stock solution of 1.0 mg/mL 2-hydroxy-6-methylpyridine-3-carboxylic acid (Aldrich, Catalog No. H43008) is prepared in de-ionized water. An internal standard working solution of 1.25 µg/mL is prepared in 0.1% formic acid from the stock solution.

C. PLP Stock and Working Solutions

All PLP solutions should be protected from exposure to light.

PLP (Sigma, Catalog No. P9255) stock solution of 1.0 mg/mL is prepared in de-ionized water. Then PLP stock solution of 5 µg/mL is prepared in 0.1% formic acid from the 1.0 mg/mL stock. Intermediate PLP standard solution of 500 ng/mL is prepared from the 5 µg/mL intermediate PLP stock solution by dilution with PLP-free plasma/serum (Biocell Labs, Carson, CA, Catalog No. 1131-00). The analyte-stripped, delipidized and defibrinated plasma/serum from Biocell is checked before use to be sure of PLP-free.

PLP working standards are prepared by serial dilution of the 500 ng/mL PLP standard solution in PLP-free plasma/serum (Biocell Labs, Carson, CA, Catalog No. 1131-00), as indicated in the table below. These working standards are used to generate the PLP standard curve illustrated in FIG. 3.

| Target Concentration (ng/mL) | Serum Standard (uL) | Biocell Plasma/Serum (uL) |
|---|---|---|
| Blank | 0 | 200 |
| S1 = 2 | 200 of S2 | 200 |
| S2 = 3.91 | 200 of S3 | 300 |
| S3 = 7.82 | 200 of S4 | 200 |
| S4 = 15.63 | 200 of S5 | 200 |
| S5 = 31.25 | 200 of S6 | 200 |
| S6 = 62.5 | 200 of S7 | 200 |
| S7 = 125 | 200 of S8 | 200 |
| S8 = 250 | 200 of intermediate PLP standard solution | 200 |

Example 2. Sample Purification

The process from sample injection to the column to chromatogram is an integrated process involving HTLC for online extraction, purification and supplying the desired analytes to the HPLC column, HPLC for analytical separation of the analytes and mass spectrometry for compound identification and acquiring specific mass to charge ratio for each analyte. As unbound and unwanted debris is swept through the extraction column at high velocity, the PLP, as well as the internal standard, is captured and concentrated in the column. The HTLC extraction column is then backflushed and the sample is loaded onto an HPLC analytical column. The analytical column is then subjected to an elution gradient. The columns are online and allow for the chromatographic separation of the components of interest. The purification process is described in further details below.

200 µL of plasma samples, including standard, control, blank and unknown, are mixed with 0.6 mL of internal standard working solution in 0.1% formic acid before online extraction. Pour the samples individually into a 96-well plate and cover. Place the 96-well plate into autosampler cooling unit. Then 10±2 µl of the sample is injected into the Cohesive TX-4 HTLC system.

The HTLC system is logically divided into two functions: 1) Solid phase extraction using a large particle size (e.g., 50 µm) packed column and 2) HPLC chromatography using a binary gradient and a 3.5 µm reverse phase analytical column. In this example, a Cohesive Cyclone® Max 0.5×50 mm column (Cohesive Technologies, Catalog No. 952980) was used for extraction. The extraction column is a mixed mode anion exchange polymer column with 0.5 (ID)×50 mm, 50µ particle size. The extraction column retains PLP, the internal standard and smaller molecules, while allowing larger molecules and electrolytes be eluted out of the column.

In the chromatography process, the gradient was started with pumping 100% deionized water at 0.4 mL/minute on the HTLC column and 5% acetic acid at 0.4 mL/minute on the HPLC column for 60 seconds. The sample was injected at the same time as the gradient began. Subsequently, the HTLC column was washed with 100% deionized water for 50 seconds, followed by 5% aqueous acetic acid for 40 seconds, at a high (about 1.5 mL/minute) flow rate. The high flow rate creates turbulence inside the extraction column. This turbulence ensures optimized binding of PLP to the large particles in the column and the passage of residual protein and debris to waste.

After the loading and washing steps, the sample was eluted off of the HTLC extraction column and transferred to the analytical HPLC column, with 5% aqueous acetic acid at a flow rate of 0.4 mL/minute for 200 seconds, starting at 2 minutes calculated from sample injection. The HPLC column is a C-8 column with a particle size of 3.5 µm. Such HPLC columns are commercially available. The column used in this example was Zorbax SB-C8 2.1×150 mm column (Agilent Technologies, Catalog No. 830990-906).

The elution from the HPLC column was driven by a binary gradient of 5% aqueous acetic acid/acetonitrile (45 to 15%/55 to 85%) at a flow rate of 0.4 mL/minute. The reminder of the gradient time is for column cleaning and re-equilibration with deionized water, 5% aqueous acetic acid and acetonitrile. The total duration for chromatograph is 9.0 minutes, with 4.3-minute data window for each sample. Therefore, two samples can be analyzed within the 9-minute method time when the dual channels are operated with overlapping gradients.

The selected parameters for HTLC were as follows:

| Injection volume: | 10 ± 2 µL |
| Autosampler tray temperature: | 5 ± 2° C. |
| Switch valve loop size: | 200 µL |

For the loading pumps, loading aqueous solution A is 5% acetic acid, loading organic solution B is 100% acetonitrile, and loading aqueous solution C is 100% water. For eluting pumps, eluting solution A is 5% acetic acid and eluting solution B is 100% acetonitrile. The total method duration is 9 minutes with 4.33 minutes data window for acquisition.

After elution, PLP was separated from other analytes in the sample. The separated PLP was then transferred to the MS/MS for quantification.

Example 3. Sample Analysis

The detection was accomplished by electrospray triplequad MS-MS system (Thermo Finnigan TSQ Quantum Ultra). The flow of liquid solvent from the analytical column entered the heated nebulizer interface of the MS/MS analyzer. The solvent/analyte mixture was first converted to vapor in the heated tubing of the interface. The analytes, contained in the nebulized solvent, were ionized and a positive charge added by the corona discharge needle of the interface, which applies a large voltage to the nebulized solvent/analyte mixture. The ions passed through the orifice of the instrument and entered the first quadrapole. Quadrapoles 1 and 3 (Q1 and Q3) were the mass filters, allowing selection of ions based on their mass to charge ratio (m/z). Quadrapole 2 (Q2) was the collision cell, where ions were fragmented by collision with argon molecules.

The first quadrapole of the MS/MS (Q1) selected for PLP with an m/z of 248.03 or the internal standard of 154.04. Ions with these m/z values passed to the collision chamber (Q2), while ions with any other m/z collided with the sides of the quadrapole and were destroyed. Ions entering Q2 collided with neutral gas molecules. This process is called Collision-Induced Dissociation (CID). The CID gas used in this example was argon. The daughter ions generated were passed into quadrapole 3 (Q3), where the daughter ions of PLP (m/z 150.00) or those of the internal standard (m/z 136.00) were selected for, while other ions were screened out. The selected daughter ions were collected by the detector. Quantification is based on peak area ratio of analytes over the internal standard acquired by selective reaction monitoring (SRM) in positive mode.

Selected MS/MS parameters were:

| | |
|---|---|
| Scan type: | positive ion SRM |
| Run time: | 4.5 ± 0.2 minutes |
| MS/MS transitions: | PLP (248.03 parent ion to 150.00 daughter ion) internal standard (154.04 parent ion to 136.00 daughter ion) |

MS common parameters:

| | |
|---|---|
| spray voltage: | 3200 |
| sheath gas: | 50 |
| aux gas: | 10 |
| capillary temperature: | 350° C. |
| tube lens offset: | 63 |
| collision energy: | 10 |
| scan width: | 0.002 |
| scan time: | 0.1 |
| Q1 resolution: | 0.2 |
| Q2 resolution: | 0.7 |

As ions collide with the detector, they produce a pulse of electrons. The pulse was converted to a digital signal, which was counted to provide an ion count. The acquired data was relayed to the computer, which plotted counts of the ions collected vs. time. Heights of the peaks generated were computer-measured, response factors were generated from calibration material, and PLP thereby quantified in the sample.

Example 4. Determination of Sample Concentration

Calculations of the unknown concentration are based on peak area ratios of PLP over the internal standard against a standard curve using LCquan software in Xcalibur (Thermo Finnigan). The peak area ratios of the daughter ions for PLP and the internal standard were used for calculations.

First, a calibration standard curve is plotted using 8 PLP standards, at 2 ng/mL, 3.91 ng/mL, 7.82 ng/mL, 15.63 ng/mL, 31.25 ng/mL, 62.5 ng/mL, 125 ng/mL and 250 ng/mL, respectively. A blank plasma/serum as zero standard is usually included each time. The software uses peak area ratio of PLP over the internal standard for data reduction. The math model of linear regression with 1/x weighting is used for data reduction. The peak area ratios of PLP vs. the internal standard is plotted against the known PLP concentrations to obtain the standard curve. An acceptable calibration curve must have a correlation coefficient (R 2) of 0.9950 or better.

To determine the concentration of PLP in a sample, the peak area ratio of PLP in the sample over the internal standard is established by the LC/MS/MS method, and then integrated to the standard curve by LCquan software.

CITED PUBLICATIONS

Each of the following publications as well as each publication cited above is incorporated herein, in its entirety, by reference.
1. Talwar et al., "Pyridoxal phosphate decreases in plasma but not erythrocytes during systemic inflammatory response," Clinical Chemistry 49: 515-518, 2003
2. Bisp et al., "Determination of vitamin B6 vitamers and pyridoxic acid in plasma: development an devaluation of a high-performance liquid chromatographic assay," Anal. Biochem. 305: 82-89, 2002
3. Bailey et al., "High performance liquid chromatography method for the determination of pyridoxal-5-phosphate in human plasma: how appropriate are cut-off values for vitamin B6 deficiency?" Eur. J. Clin. Nutr. 53: 448-455, 1999
4. Kimura et al., "Highly sensitive and simple liquid chromatographic determination in plasma of B6 vitamers, especially pyridoxal 5'-phosphate," J. Chromatogr A. 722: 296-301, 1996
5. Edwards et al., "A simple liquid-chromatographic method for measuring vitamin B6 compounds in plasma," Clin. Chem. 35: 241-245, 1989
6. Botticher et al., "A new HPLC-method for the simultaneous determination of B1-, B2- and B6-vitamers in serum and whole blood," Int. J. Vitam. Nutr. Res. 57: 273-278, 1987
7. Ubbink et al., "Stability of pyridoxal-5-phosphate semicarbazone: applications in plasma vitamin B6 analysis and population surveys of vitamin B6 nutritional status," J. Chromatogr. 342: 277-284, 1985
8. Schrijver et al., "Semi-automated fluorometric determination of pyridoxal-5'-phosphate (vitamin B6) in whole blood by high-performance liquid chromatography (HPLC)," Int. J. Vitam. Nutr. Res., 51: 216-222, 1981
9. Hachey et al., "Quantitation of vitamin B6 in biological samples by isotope dilution mass spectrometry," Anal. Biochem. 151: 159-168, 1985
10. Midttun et al., "Multianalyte quantification of vitamin B6 and B2 species in the nanomolar range in human plasma by liquid chromatography-tandem mass spectrometry," Clin. Chem., 51: 1206-1216, 2005
11. Zimmer et al., J. Chromatogr. A 854: 23-35 (1999)
12. U.S. Pat. No. 5,968,367
13. U.S. Pat. No. 5,919,368
14. U.S. Pat. No. 5,795,469

15. U.S. Pat. No. 5,772,874
16. P. S. Bernard & J. M. Wallace, "Turbulent Flow Analysis: Measurement and Prediction," John Wiley & Sons, Inc. (2000)
17. Jean Mathieu & Julian Scott, "An Introduction to Turbulent Flow," Cambridge University Press (2001)
18. U.S. Pat. No. 6,204,500
19. U.S. Pat. No. 6,107,623
20. U.S. Pat. No. 6,268,144
21. U.S. Pat. No. 6,124,137
22. Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999)
23. Merchant and Weinberger, "Recent advancements in surface-enhanced laser desorption/ionization-time of flight-mass spectrometry," Electrophoresis 21: 1164-67 (2000)
24. Rybak et al., "Clinical vitamin B6 analysis: an interlaboratory comparison of pyridoxal 5'-phosphate measurements in serum," *Clinical Chemistry* 51:1223-1231 (2005)

What is claimed is:

1. A method for detecting the presence or amount of pyridoxal 5'-phosphate in a sample by tandem mass spectrometry, comprising:
   (i) adding an internal standard to a sample, wherein the internal standard is 2-hydroxy-6-methylpyridine-3-carboxylic acid;
   (ii) purifying the sample with an extraction column and an analytical column for chromatographic separation;
   (iii) ionizing pyridoxal 5'-phosphate and the internal standard in the sample to generate a parent ion of pyridoxal 5'-phosphate and a parent ion of the internal standard;
   (iv) generating one or more daughter ions of said parent ions, wherein said one or more daughter ions comprise a daughter ion of pyridoxal 5'-phosphate and a daughter ion of the internal standard; and
   (v) detecting the presence or amount of one or more said ions generated in step (iv), and determining the presence or amount of said pyridoxal 5'-phosphate in said sample from the presence or amount of one or more said ions.

2. The method of claim 1, wherein said sample comprises plasma.

3. The method of claim 1, wherein said ionization is performed by electrospray ionization.

4. The method of claim 1, wherein step (iii) is performed by Collision-Induced Dissociation using a neutral gas.

5. The method of claim 1, further comprising protein precipitation.

6. The method of claim 1, wherein the parent ion of pyridoxal 5'-phosphate has a mass/charge ratio of 248.03+/−1.

7. The method of claim 1, wherein the parent ion of the internal standard has a mass/charge ratio of 154.04+/−1.

8. The method of claim 1, wherein the daughter ion of pyridoxal 5'-phosphate has a mass/charge ratio of 150.00+/−1.

9. The method of claim 1, wherein the daughter ion of the internal standard has a mass/charge ratio of 136.00+/−1.

10. The method of claim 1, wherein the ionization is in positive ion mode.

* * * * *